(12) United States Patent
Fuchs et al.

(10) Patent No.: US 10,697,954 B2
(45) Date of Patent: Jun. 30, 2020

(54) SAMPLE-HOLDING ELEMENT, ANALYSIS SET, AND METHOD FOR ANALYZING A LIQUID, IN PARTICULAR A COOLING LUBRICANT EMULSION

(71) Applicant: Fuchs Petrolub SE, Mannheim (DE)

(72) Inventors: Christine Fuchs, Düsseldorf (DE); Heinz Gerhard Theis, Westheim (DE)

(73) Assignee: Fuchs Petrolub SE, Mannheim (DE)

( * ) Notice: Subject to any disclaimer, the term of this patent is extended or adjusted under 35 U.S.C. 154(b) by 0 days.

(21) Appl. No.: 16/345,254

(22) PCT Filed: Jul. 28, 2017

(86) PCT No.: PCT/EP2017/000917
§ 371 (c)(1),
(2) Date: Apr. 26, 2019

(87) PCT Pub. No.: WO2018/077449
PCT Pub. Date: May 3, 2018

(65) Prior Publication Data
US 2019/0293622 A1  Sep. 26, 2019

(30) Foreign Application Priority Data

Oct. 26, 2016 (EP) .................................... 16002281

(51) Int. Cl.
*G01N 21/03* (2006.01)
*G01N 33/28* (2006.01)
(Continued)

(52) U.S. Cl.
CPC ............ *G01N 33/2894* (2013.01); *B01L 3/00* (2013.01); *G01N 21/01* (2013.01); *G01N 21/03* (2013.01);
(Continued)

(58) Field of Classification Search
CPC ............... G01N 33/2888; G01N 21/03; G01N 2021/0346; G01N 27/06; G01N 27/02
See application file for complete search history.

(56) References Cited

U.S. PATENT DOCUMENTS 6,097,479 A    8/2000  Melendez et al.
2003/0034740 A1 *  2/2003  Coll ........................ G01N 21/31
315/111.21
(Continued)

FOREIGN PATENT DOCUMENTS

DE  197 04 320   9/1997
DE  696 34 490   3/2006
(Continued)

*Primary Examiner* — Maurice C Smith
(74) *Attorney, Agent, or Firm* — Gudrun E. Huckett

(57) ABSTRACT

The invention relates to a sample-holding element (20) for a liquid sample for the simultaneous analysis of three or more chemico-physical parameters of the liquid by means of an analysis device. The sample-holding element (20) has a sample-holding chamber (31), which can be filled with the liquid, wherein the sample-holding element (20) has at least three measurement points (24, 25, 26, 26N, 27) arranged adjacent to each other, which are distributed over the sample-holding chamber (31), wherein two of the measurement points (24, 25) are a photonic measurement point (24) and a refractive-index measurement point (25) and wherein the at least one further measurement point is selected from the group comprising at least a pH measurement point (26), a conductivity measurement point (27) and a germ measurement point. The sample-holding element (20) is a planar element (20) that is double-walled at least in some sections and that has plates (30, 30'), which are arranged on each other in a plane-parallel manner and are connected to each other at the edges thereof at least in some sections, wherein the sample-holding chamber (31) is formed as a planar gap between the plates (30, 30') and the distance between the
(Continued)

plates (30, 30') is just so large that the liquid sample can be subjected to the capillary effect between the double walls (30, 30'). The measurement point (25) for measuring the refractive index has a refraction structure (25', 25") on one of the plates (30, 30') in a region predefined therefor. The invention further relates to an analysis device set having the sample-holding element (20) and having an analysis apparatus (1) and to a method for the simultaneous analysis of three or more chemico-physical parameters of the liquid.

24 Claims, 7 Drawing Sheets

(51) Int. Cl.
  *G01N 21/01* (2006.01)
  *B01L 3/00* (2006.01)
(52) U.S. Cl.
  CPC .......... *G01N 2021/0346* (2013.01); *G01N 2021/0367* (2013.01); *G01N 2021/0378* (2013.01); *G01N 2021/0389* (2013.01)

(56) References Cited

U.S. PATENT DOCUMENTS

| | | |
|---|---|---|
| 2010/0157303 A1 | 6/2010 | Ono |
| 2011/0201099 A1 | 8/2011 | Anderson et al. |
| 2011/0236262 A1 | 9/2011 | Horii et al. |
| 2012/0123686 A1* | 5/2012 | Xiang .............. G16H 40/63 702/19 |
| 2013/0330245 A1 | 12/2013 | Duncan et al. |
| 2015/0309008 A1* | 10/2015 | Adelman .......... H04W 12/02 356/72 |

FOREIGN PATENT DOCUMENTS

| | | |
|---|---|---|
| DE | 10 2010 028 319 | 11/2011 |
| JP | 2012202807 | 10/2012 |
| WO | 97/21090 | 6/1997 |
| WO | 00/13002 | 3/2000 |
| WO | 2015/192855 | 12/2015 |

* cited by examiner

A - A

SAMPLE-HOLDING ELEMENT, ANALYSIS SET, AND METHOD FOR ANALYZING A LIQUID, IN PARTICULAR A COOLING LUBRICANT EMULSION

BACKGROUND OF THE INVENTION

The invention relates to a sample-holding element for a liquid sample, an analysis device set for simultaneous analysis of three or more chemical and physical parameters of liquids that comprises an analysis apparatus designed as a hand-held device and the sample-holding element for the liquid sample, the use of the set, and a method that is implemented using the analysis apparatus and the sample-holding element.

The prior art knows measuring devices that can be used to measure or check various parameters of cooling lubricants. Accordingly, refractometers for determination of the refractive index of the cooling lubricant are known. In the case of water-mixed cooling lubricants, the mixing ratio can be deduced from the refractive index. Moreover, measuring devices for determination of the electric conductivity are known, in which the resistance is determined via a certain measuring section. Measuring devices for determination of the pH value of the cooling lubricants are available as well. Essentially, two types of pH-measuring devices are used in this context: pH meters with electrode and optochemical pH measuring devices.

Moreover, there are measuring devices available that can determine different parameters after prior selection of the measuring parameter.

Accordingly, DE 10 2010 028 319 discloses a method for controlling the concentration of water-mixed cooling lubricants, in which a refractometer is used for determination of the refractive index of the cooling lubricant and the electrical conductivity is recorded through a resistance measurement, with its reciprocal resulting in the conductivity. Moreover, the temperature of the cooling lubricants is monitored in order to take into account the changes of the data arising from temperature fluctuations. The measured parameters are used to draw conclusions concerning the composition of the cooling lubricant and the composition is adapted in case of need.

DE 696 34 490 T2 discloses a disc-shaped microsystem platform with two flat planar surfaces as sample-holding element for a liquid sample. The disc-shaped microsystem platform comprises input ports for a liquid sample, liquid micro-channels, reaction and detection chambers, wherein multiple measuring points are provided on the disc for analysis of the liquid sample. The measurements that can be done comprise luminescence measurements and refractive index measurements as well as electrochemical detection methods. The corresponding analysis device is fitted, similar to a CD player, with elements for rotating and reading the disc-shaped microsystem platform for controlling the functions. After application of the analyte to be tested into the input ports, the microsystem platform is inserted into the CD player device, wherein the liquid transport through the micro-channels on the disc takes place by means of centripetal acceleration in the CD player device and by selective activation of valves on the disc. The results of the analysis can be saved and/or displayed immediately to the user.

A sample cassette with channels and chambers that can comprise electrodes and detection windows for optical measurements is known from US 2011/201099 A1. Reagents such as binding reagents, detectable markers, sample preparation reagents, washing solutions, buffers, etc., in liquid or solid form or on the surface of fixed immobilised phase carriers can be present in the chambers. The corresponding analysis apparatus, which is not provided as a hand-held device, comprises appropriate detectors and means for accommodating the cassette and for positioning the cassette as well as electrical systems for contacting the electrodes of the cassette as well as control systems for detecting, processing, and saving the signals of the detectors for the intended measurements. For luminescence measurements, the analysis apparatus comprises an area that is closed in light-tight manner. For accommodation and positioning of the sample-holding element, the analysis apparatus comprises a cassette compartment that is mounted on rails via a guide sled in order to enable a motor-driven motion of the compartment into and out of the area that is closed in light-tight manner.

US 2013/330245 A1 describes a sample-holding element with channels and a detection chamber for optical measurements as well as electrodes at the fluid inlet for measurement of the resistance of the sample in order to signal sufficient immersion of the sample-holding element into the liquid to be tested during the sampling. For sampling, the sample-holding element is inserted into the corresponding analysis apparatus, which is designed as a hand-held device and can accommodate multiple sample-holding elements simultaneously for analysis of multiple parameters, and comprises corresponding optical analysis devices, etc. During the sampling, a liquid sample is drawn into the sample-holding element by a pump of the analysis device.

Based on said prior art, it is the object of the present invention to devise an improved device by means of which a liquid—such as a cooling lubricant—can be prepared with minimised sample volume needs for measurement of the concentration of the liquid or its components and for measurement or determination of multiple further parameters such as the refractive index and the temperature and, optionally, even further parameters that are characteristic of the nature of the fluid, while keeping the handling as simple as possible.

SUMMARY OF THE INVENTION

Said object is met through the aid of a sample-holding element that is characterized in that
the sample-holding element is a planar element that is double-walled at least in sections and has planar-parallel plates arranged on top of each other that are connected to each other, wherein the sample-holding space is designed in the form of a gap in planar manner between the two plates, and a distance between the plates is just so large that the liquid sample between the double walls can be subjected to the capillary effect, and
the measuring point for the refractive index measurement comprises a diffraction structure at one of the plates in an area predetermined for this purpose.

The further object, being to devise an improved device by means of which the concentration of a liquid, such as a cooling lubricant, and simultaneously other parameters, such as the refractive index and the temperature and, optionally, even further parameters that are characteristic of the nature of the fluid, can be measured and/or determined reproducibly and reliably directly on-site, is met by the analysis device set that is characterized in that the sample-holding element is a sample-holding element as described above and the analysis apparatus comprises an optoelectronic analysis device and a data processing unit that is connected in communicative manner to the analysis device and the display device, wherein the optoelectronic analysis device comprises at least three measuring devices in an adjacent arrangement with respect to each other, whose arrangement matches the arrangement of the measuring points on the sample-holding element.

The even further object, being to devise an improved and simultaneously simplified measuring method for analysis of more than three parameters of the liquid, such as a cooling lubricant, on-site, is met by the method comprising the steps of immersing the sample-holding element into the liquid or contacting an opening of the sample-holding element that is formed by the non-connected parts of the edge to the liquid surface, and filling the sample-holding space of the sample-holding element with a sample of the liquid through the action of the capillary effect between the double walls of the sample-holding element, completely inserting the sample-holding element into the analysis apparatus, starting and carrying out at least three or more measuring processes simultaneously by means of the measuring devices at the measuring points, after completion of the measuring processes, displaying the measuring results on the display facility.

Developments and preferred embodiments of the devices and method are specified in the sub-claims.

A first embodiment of the sample-holding element according to the invention for a liquid sample, such as, for example, a cooling lubricant, for simultaneous analysis of three or more chemico-physical parameters of the liquid, i.e. quasi characteristics thereof, by means of an analysis device, mainly in order to determine the concentration of at least one ingredient, comprises, aside from a sample-holding space that can be filled with the liquid, at least three measuring points that are arranged adjacently to each other with one of these being a photonic measuring point (this term summarising measuring points for absorption and photoluminescence) and another one being a refractive index measuring point.

Moreover, the sample-holding element comprises at least one further measuring point, which can, for example, be a pH measuring point, a conductivity measuring point or a germ measuring point. All measuring points are distributed throughout the sample-holding space, meaning that certain areas of the sample-holding space each form a measuring point such that the measuring points are in fluid contact with the liquid when liquid is taken up into the sample-holding space of the sample-holding element.

Accordingly, "measuring point" shall refer to a predetermined area of the sample-holding space that is designed appropriately for the measurement on the liquid intended to be done in this place. If the intended measurement includes an optoelectronic measurement device, for example for detection of photoluminescence, by means of which light is directed at the predetermined area of the sample-holding space and luminescence emitted by the liquid is detected, the measuring point of the sample-holding element comprises correspondingly transparent windows on both sides of the sample-holding space in the corresponding area touched directly by the liquid (at the windows). In another example, in which the measurement to be done is intended to determine the conductivity via the electrical resistance of the liquid, electrodes extend all the way into the sample-holding space, wherein the measuring point is formed by the distance ("measuring section") between the electrodes, which is in direct contact with the liquid when the sample-holding space is filled.

For the adjacent arrangement of multiple measuring points, the sample-holding element according to the invention is a planar element that is designed to be double-walled and to have planar-parallel plates arranged on top of each other that are connected to each other, at least in sections, at their edges. In this context, referring to the refractive index measuring point, one of the plates comprises in the area predetermined for this purpose, preferably on the inside of the plate, a diffraction structure by means of which light beams, which enter through the other plate and cross the sample-holding space (and the liquid contained therein), are diffracted in a predetermined manner. In this context, the sample-holding space is designed as a gap and in planar manner between the plates, wherein the distance between the double walls is just sufficient such that a liquid sample can be drawn into the sample-holding space by means of the capillary effect at at least one point, at which the plates are not connected to each other on the edges. In the case of aqueous emulsions with a water content of at least 20%, said distance can be in the range of 0.5 to 2 mm, preferably approximately 1 mm. If a liquid to be analysed has a deviating water content or a deviating viscosity, a sample-holding element with a correspondingly adapted distance between the plates is designed in order to still attain the filling of the sample-holding space by capillary forces alone. Accordingly, it is sufficient to immerse the sample-holding element, by the opening formed by the non-connected parts of the edge, into the liquid to be tested and/or to contact the liquid surface—since complete immersion is not required—whereupon the liquid sample flows into the sample-holding space through the action of the capillary effect. This is a very suitable procedure especially for fluids such as cooling lubricants. Advantageously, due to the solely passive filling by the capillary effect, no aids are required for transitioning the liquid sample into the sample-holding space of the sample-holding element, which is the case according to the prior art, in which either pipettes are used for sampling and filling the sample-holding element, which then performs a rotary motion in order to transition the liquid to the measuring points, or sample-holding elements are used that need to be connected to a pump in order to draw the liquid into the sample-holding space and to the measuring points.

As an advantageous result, an extremely low sample volume is sufficient for measurement of a multitude of at least three, rather four or more, different chemico-physical parameters.

Designed as a planar element, the sample-holding element can particularly suitably be a flat elongated sample strip with a total thickness in the range of 2 to 8 mm, preferably in the range of 2.5 to 6 mm and particularly preferably in the range of 2.5 to 4.5 mm.

For designing the smallest possible sample-holding element in this context, it is important to note that the measuring points are situated as close as possible to each other, basically on a fluid path that leads from the inlet opening, which can be designed to be gap-like—multiple inlet openings can be present just as well—along the measuring points to an outlet point designed as a ventilation channel with air exit opening at which the plates are not connected to each other either.

For convenience of the filling process, the plates are preferably not connected to each other at least along a side of the planar sample-holding element, which is in particular designed as an elongated sample strip, such that a filling gap for the liquid is being provided. Preferably, this can be a long side of the sample strip, since the longer filling gap allows a markedly shorter filling time of the sample-holding space to be attained than is possible with a filling gap at a short side.

Accordingly, a narrow thin test strip made of two small plates can be devised, wherein the small plates are not connected and/or glued to each other on the edge in one or more places on a long side of the test strip, and wherein the interior thereof forms a thin gap, such as a channel, that guides the liquid and has the measuring points situated along it, because the platelets are not glued to each other in this place either. For complete filling of the sample-holding space, the ventilation channel can extend through a short side and terminate towards the outside in order to discharge air that is displaced from the sample-holding space during the sampling by ingress of the liquid.

Since the sample-holding element comprises measuring points at which optical and/or optoelectronic analytical procedures are applied, the planar element is advantageously made, at least in part—i.e. at least in the area of the measuring points designed for this purpose—of translucent material such as glass and/or quartz glass or of a transparent plastic material, such as, for example, polymethylmethacrylate or polycarbonate. However, other transparent plastic materials are conceivable as well.

For designing the measuring point for the conductivity measurement, at least two contact strips for application of voltage are arranged on a lengthened section of one of the plates that protrudes beyond the other plate and extend as electrodes up into the sample-holding space and end there while being distanced from each other by a measuring section that forms the conductivity measuring point.

According to a further embodiment, it is advantageous to have the planar element designed as a handle section for handling of the sample-holding element at an end that faces away from the end with the contact strips of the conductivity measuring point. The ventilation channel originating from the sample-holding space can extend through said handle section and can exit there at an air exit opening. Since the invention provides the handle section of the sample-holding element to partially protrude from the analysis apparatus during the measuring process in the combination with the analysis apparatus of the invention that is provided as a hand-held device, a different arrangement of a ventilation channel can be provided just as well, for example by providing it as a measuring point for a germ measurement by means of a (micro) gas sensory system. A ventilation channel originating from the sample-holding space then exits in a different place, at which its air and/or gas exit opening can communicate with a corresponding (micro) gas sensory system of an analysis apparatus.

Moreover, the handle section can be opaque, preferably be black, in order to prevent the incidence of diffracted light when the sample-holding element is inserted into the analysis apparatus. It is conceivable just as well to provide differently coloured handle sections for different sample-holding elements. A sample-holding element that is accommodated completely by an analysis apparatus can just as well be designed to be completely transparent. Moreover, a handle section can comprise a textured surface in order to ease the handling through better grip. Moreover, markings supporting the correct insertion of the sample-holding element into an analysis apparatus can be placed on the handle section—or on different suitable points of the sample-holding element. According to the lock-and-key principle, correct insertion can also be supported by special shaping of the sample-holding element, in particular at the end facing away from the handle section.

Preferably, the photonic measuring point is a luminescence measuring point and particularly preferably it is a fluorescence measuring point. For this purpose, the sample-holding element comprises, on both plates in the area intended for the measuring point, a window section that is transparent to the corresponding excitation and emission wavelengths. The two window sections of the measuring point for the luminescence measurement can be congruent.

If the sample-holding element comprises a pH measuring point, it can comprise an indicator dye-containing substrate that is arranged at a predetermined second section between the two plates, which correspondingly are, in an area that surrounds said section, transparent to the light required for the optoelectronic detection of the colour change of the indicator substrate.

Moreover, the group from which the at least one further measuring point is selected can comprise a nitrite measuring point, which can be designed comparable to the pH measuring point with regard to an optoelectronic detection of a colour change, though with a nitrite-reactive substrate. Conceivable in this context are, e.g., a primary aromatic amine that reacts with nitrous acid to form a diazonium salt, which in turn forms a coloured azo compound in the presence of amines in acidic solution, which can be detected by photometry and can be quantified by calibration. A known reagent (Lunge's reagent, photometric detection of the azo compound at 535 nm) consists of 1-naphthylethylenediamine and sulfanilic acid and possibly acetic acid. Analytical monitoring of the nitrite content of aqueous metal processing solutions or emulsions is important since nitrite can react as a reaction partner with secondary amines or alcanolamines to form carcinogenic nitrosamines. Nitrite may be introduced into the process media, i.e. the aqueous metal processing solutions or emulsions, inter alia, via the batch water for preparation of the emulsion or via the metal parts that undergo a hardening process and are still contaminated with curing salts.

For formation of the refractive index measuring point, one of the two plates can comprise, at a predetermined third section, a prism structure or a Fresnel lens structure as diffraction structure. As before, the plates are transparent at said section to the wavelengths used for the refractive index measurement. The diffraction structure provides surface sections that are at an angle with respect to the plate plane and at which impinging light beams are deflected accordingly. A prism structure consists of at least one, preferably more, structures with a triangular profile that are arranged adjacently to each other. A Fresnel lens structure comprises a series of ring-shaped steps.

In this context, the section with the prism structure and/or the Fresnel lens structure as well as the section with the indicator dye-containing substrate are constituting components for the optical, electronic, and optoelectronic analysis devices that communicate with the sample-holding element during a measurement and/or an analytical process.

In general, the sample-holding element according to the invention is designed as a measuring strip for single use.

An analysis device set, also according to the invention, for simultaneous analysis of three or more chemico-physical parameters and/or characteristics of liquids comprises an analysis apparatus designed as a hand-held device with a housing and with a display and at least one sample-holding element according to the invention for the liquid sample. In this context, hand-held device shall be understood to mean that the device is small and handy and can easily be carried by one person to the facilities using the liquid to be analysed and can be operated by hand. For the measurements to be performed on the sample-holding element, the analysis apparatus comprises an optoelectronic analysis device that comprises at least three measuring devices arranged adjacently to each other, whose arrangement corresponds to the arrangement of the measuring points on the sample-holding element. Moreover, the analysis apparatus comprises a data processing unit that is connected in communicative manner to the analysis device and the display device.

An insertion device for accommodation of the sample-holding element is situated in the housing of the analysis apparatus according to the invention, and is arranged in the housing such as to be detachable and comprises an insertion opening. The latter terminates into a recess that is designed correspondingly for accommodation of a sample-holding element. Moreover, corresponding to the arrangements of the measuring devices and measuring points and depending on the type of the respective measuring point, the insertion device comprises an optical, electronic or optoelectronic communication facility that permits a corresponding signal transmission (this shall also include light transmission) between the measuring points of a sample-holding element accommodated in the insertion device and the measuring devices.

For this purpose, the insertion device is manufactured, at least in part, from transparent material. This means that it is transparent at least at those points at which this is required for optical measurements. In general, the insertion device can be manufactured from opaque material, preferably from plastic material, particularly preferably from black plastic material, and is then insensitive to interfering light as well.

The insertion device can be designed to have a flange section comprising the insertion opening and a shell section that is arranged in the housing such as to be detachable, borders the recess, and comprises the optical, electronic or optoelectronic communication facilities. Although these are preferably designed to be window-like in the form of sections made of transparent material—because only this will prevent soiling of the internal space of the analysis apparatus—it is conceivable just as well that these communication facilities are simply formed by openings in the shell section. By means of the optical, electronic or optoelectronic communication facilities, the components of the analysis apparatus and of the sample-holding element can interact in order to facilitate the analysis of the chemico-physical parameters to be determined. Referring to the refractive index measurement, for example, the section with the prism structure and a corresponding light source communicate with each other appropriately via a window in the insertion device such that light passing through the window and through the liquid accommodated in the sample-holding space impinges on and is diffracted by the section with the prism structure. A further window on the other side of the insertion device then facilitates the communication with a sensor of the analysis apparatus for determination of the refraction angle.

Two of the measuring devices of the analysis apparatus are a photonic measuring device, preferably a luminescence measuring device, particularly preferably a fluorescence measuring device, which is used with fluorescence markers in the liquid for measuring the concentration of one or more, possibly different, components of the liquid, and one refractive index measuring device. The luminescence measuring device comprises an excitation light source with a suitable wavelength for excitation of the fluorescence marker, and a suitable sensory system for measuring the emitted fluorescence. With the exception of the prism structure, which is part of the sample-holding element as has been mentioned above, the refractive index measuring device of the analysis apparatus comprises all other requisite components of the refractometer, such as light source and sensory system.

Analogous to the at least one further measuring point of the sample-holding element, the analysis apparatus comprises at least one further measuring device that is selected from the group such as to match the measuring points of the sample-holding element. This can, for example, be a pH measuring device, which preferably is designed as a pH optode, wherein the optical effect of the colour change of the indicator substrate upon contact with the liquid to be tested is being utilised. If an indicator paper is used as the indicator substrate, a measuring device detecting the colour of light reflected by the indicator paper is being utilised.

Preferably, a universal indicator with a mixture of multiple indicator substances differing in colours and colour change ranges can be used, wherein these are appropriately matched such that pH values in a wide pH range can be detected by different colour changes.

If the sample-holding element comprises a nitrite measuring point for detecting nitrite and/or for measuring the nitrite content, an analysis apparatus appropriately fitted with a nitrite measuring device must be used for analysis.

Accordingly, a light source unit each, which shall comprise not only the light source, but also, if applicable, requisite optical components such as filters, lenses, etc., as well as a detection unit (possibly also comprising optical components such as filters, lenses, etc., and the actual detector) is provided for the luminescence measuring device and the refractive index measuring device as well as for the pH measuring device and the nitrite measuring device. The various measuring devices can comprise different light sources and detectors, which are selected according to the measuring principle—said selection is known to a person skilled in the art. In the analysis apparatus, the light source units of the various measuring devices can be arranged on the one side of the sample-holding element and/or of the insertion device, and the detector units can be arranged on the other side. Due to a matching arrangement and/or the use of matching optical components, the beam paths between the light sources and the detectors are such that the light beams pass through the sample-holding element at the respective measuring points (luminescence and refraction) or are reflected there (pH).

As a measuring device that is an alternative or addition to the pH measuring device, an analysis apparatus can just as well comprise a conductivity measuring device, which actually is a resistance measuring device, in which the conductivity of the liquid is determined from the measured resistance. As before, the sample-holding element with the contact strips comprises a part of the measuring device. The conductivity measuring device of the analysis apparatus comprises a frequency generator with contact elements, which, after arranging the sample-holding element in the analysis apparatus, are in direct or indirect electrical contact with the at least two contact strips of the sample-holding element by means of contact bridge elements.

For detection of the germ load of the liquid, the analysis apparatus can comprise a corresponding measuring device, which can be a so-called "electronic nose", which is formed from at least one microelectronic gas sensor, usually from a plurality of gas sensors, since germs produce volatile organic compounds that transition from the liquid into the vapour phase and can be detected by the gas sensors, when said vapour phase is made to be connected to the sensors. For this purpose, the ventilation channel of the sample-holding element can be connected to the electronic nose by means of a connecting line of the analysis apparatus. The connecting line can also lead to the filling gap—a correspondingly gas-permeable window in at least one of the plates through which the volatile compounds get to the gas sensors via the connecting line is also conceivable as germ measuring point. In order to obtain a directed influx of the volatile compounds to the gas sensors, the use of a micro-fan is conceivable; a directed guidance of the flow can also be supported through a special design of the ventilation channel and connecting line in terms of the design of the cross-section.

Since the refractive index, in particular, is temperature-dependent, the analysis apparatus comprises a temperature measuring device that is connected to the data processing unit such that the influence of the temperature can be compensated for during the measurement of the refractive index. The temperature sensor used in this context can, for example, be a resistance thermometer, which can be accommodated easily in the housing of the analysis apparatus, which is designed as a hand-held device, due to its small dimensions.

Soiling of the sensitive measuring technology on the inside of the analysis apparatus is prevented by the insertion device described above, which separates the inserted sample-holding element from the internal space of the analysis apparatus whose housing is designed to be correspondingly fluid- and dust-tight. In an analytical arrangement, in which the insertion device is inserted into the housing, the flange section of the insertion device of a preferred embodiment touches, on the outside, against an edge of the housing and frames a cover plate, in which the insertion opening has been made. Said insertion opening can be sealed by a sealing lip and/or a pair of sealing lips such that any liquid that may be present on the outside of the sample-holding element is stripped off during the insertion and therefore does not ingress into the analysis apparatus. The sealing lip(s) are held in the flange section by the cover plate, wherein the cover plate is fastened in and/or screwed into the flange section in detachable manner. It is also feasible in this context that the screws are designed not only for fastening the cover plate in the flange section, but penetrate through the flange section and thus simultaneously effect the detachable fastening of the insertion device to the housing of the analysis apparatus. However, other fastening variants of the cover plate both in the flange section and in the insertion device in the analysis apparatus are conceivable as well; accordingly, plug-in, clamping or snap-in systems are conceivable as well.

As an alternative to the direct contacting of the contact strips of the sample-holding element to the contact elements of the frequency generator for the conductivity measurement, the invention can provide the insertion device to comprise contact bridges that establish the contact of the contact element of the analysis apparatus to the at least two contact strips of the sample-holding element, when the latter is arranged in the insertion device in the arrangement for analysis.

The contact bridges and/or contact elements of the analysis apparatus can be designed as contact springs and/or spring contact bar in order to provide for secure contacting to the contact strips of the inserted sample-holding element.

The frequency generator and all other electrical consumers of the analysis apparatus, such as the optoelectronic analysis device, the data processing unit, and the display facility as well as the thermal sensor, etc., are connected to an energy source, which is also accommodated in the housing of the analysis apparatus. The energy source can preferably be a rechargeable battery that can be recharged via an interface in the housing. If applicable, the analysis apparatus can just as well comprise on its outside one or more solar cells for recharging the rechargeable battery.

The display facility can be designed as a touch-sensitive display facility (also called touch-screen display hereinafter) and can thus simultaneously be an operating interface for transmitting user input via the communication line to the data processing unit. Same can comprise or be connected to an external communication interface that can be a connector interface, such as, e.g., USB or micro USB interface or a radio interface, in particular a local area radio interface, for example according to the Bluetooth® standard, etc.

Another subject matter according to the invention is a method for simultaneous in situ analysis of at least three different chemico-physical parameters of a liquid through the use of an analysis device set according to the invention. The process comprises the steps of:

immersing the sample-holding element into the liquid or contacting an opening of the sample-holding element that is formed by the non-connected parts of the edge to the liquid surface, and filling the sample-holding space of the sample-holding element with a sample of the liquid to be tested through the action of the capillary effect between the double walls of the sample-holding element, for the purpose of which the filling opening is immersed into the liquid for a predetermined period of time that depends on the dimensions of the sample-holding space and of the filling opening;

complete insertion of the sample-holding element into the analysis apparatus;

starting and carrying out at least three or more measuring processes simultaneously by means of the measuring devices at the measuring points;

after completion of the measuring processes, displaying the measuring results on the display facility.

Advantageously, in a development of the method, a liquid to be tested can be selected from various testable liquids that are deposited in a database that is stored in the data processing unit or on a storage medium connected to it, and that are presented in a selection menu through a user input on the display facility, which can suitably be designed as a touch-screen display.

However, it is also feasible, in general, to design the analysis apparatus for a certain type of liquid in order to devise a particularly simple device for a very specific application case such that no selection of liquid needs to take place.

Also optionally, developments of the method can provide for displaying on the display facility a prompt for removal of the sample-holding element from the analysis apparatus after completion of the measuring processes. The removal is detected by the software after the measuring process is completed. When the sample-holding element is being inserted, though, the end position is detected optoelectronically and the analysis and data capture are then started, which can take place automatically or through a user input. Lastly, according to the invention it is also feasible, after the removal of the sample-holding element from the analysis apparatus has been detected, to display the measuring results on the display facility and to store and/or transfer them to further devices.

The storage can take place in an internal memory of the data processing unit or on a removable storage medium connected to it, such as an SD card or a USB stick. The transmission of the measuring results to a preset receiver can preferably take place by means of the radio interface, but just as well in wired manner by means of a corresponding USB cable.

Embodiments of the method relate to the calibration of the analysis apparatus for the liquids that can be tested and are deposited in the database and/or the input of new liquids with the analysis apparatus and addition of the inputted liquids to the database.

Both, calibration and input, each take place through selection and confirmation of corresponding fields that are displayed in the selection menu, wherein calibration solutions with known chemico-physical parameters are provided for calibration of the measuring devices. For the input of new liquids, these liquids are provided as liquids to be tested that have known chemico-physical parameters.

As before, the liquid in the method is a liquid that comprises at least one marker substance that can be detected by means of luminescence analysis, wherein one of the measuring points is a luminescence measuring point.

In particular, the method can be applied through the use of an analysis device set according to the invention for analysis of a metal processing liquid, in particular a cooling lubricant, mainly a cooling lubricant emulsion, as liquid, wherein at least one first marker substance that can be detected by luminescence analysis is added to the liquid at a predetermined concentration such that the luminescence measurement allows conclusions to be made concerning the concentration of a liquid ingredient, in particular the concentration of the cooling lubricant, in the emulsion.

For determination of the cooling lubricant concentration of an emulsion by means of luminescence analysis, the marker substance is added to the cooling lubricant emulsion at a predetermined concentration. The molar concentration of the marker or marker composition, which can just as well be composed of multiple markers, is $10^{-5}$ to $10^{-6}$ mol/litre in the cooling lubricant concentrate and/or $10^{-7}$ to $10^{-8}$ mol/litre in the application concentration, i.e. in the cooling lubricant emulsion. Said dosage refers, inter alia, to dyes based on perylene chemistry. The luminescence marker added to the liquid for measuring the concentration can be a dye that is non-visible or visible to the naked eye.

Preferably, a marker can be used that is made up of at least two dye molecules from the series of the rylene dyes, e.g. perylene and quaterrylene, or any combination of rhodamine carbonyl derivatives and acridine derivatives such that at least two long-wave measuring ranges can be covered. Measuring errors can be minimised by measuring in two measuring ranges simultaneously.

If the liquid is a cooling lubricant emulsion for special manufacturing purposes, a booster can be added to increase the performance. This is usually done using a fraction of less than 5% by weight relative to the total weight of the cooling lubricant emulsion. During small-scale production of components with machine tools that are not really intended for small-scale production, such boosters need to be used in order to maintain the quality of the small-scale production and to improve the performance of the cooling lubricant in order to avoid having to develop a special cooling lubricant for these applications, which would be uneconomical. In these cases, it is particularly advantageous to be able to use an additional added marker that is characteristic of the booster to readily determine the concentration of the booster under in situ conditions using the sample-holding element according to the invention and the analysis apparatus included in the set. Previously, this could be detected only in the laboratory by means of infrared spectroscopy for detection of the ester band (if the booster contains an ester compound) and/or by x-ray fluorescence analysis for detection of sulfur/phosphorus compounds of the booster.

Accordingly, the method according to the invention also relates to the liquid comprising a booster additive and to at least one second marker substance that can be detected by means of luminescence analysis being added to the liquid at a predetermined concentration, wherein the second marker substance differs from the first marker substance with regard to its luminescence properties, such that the luminescence of the first marker allows conclusions to be made concerning the concentration of a first ingredient, e.g. the cooling lubricant in the emulsion, in the luminescence analysis and the luminescence of the second marker allowing conclusions to be made concerning the concentration of the booster additive.

The marker selection is guided in suitable manner with a view to a balance between oleophilic and hydrophilic properties. If only the booster is labelled, the marker stays in the booster in the application and does not diffuse into the basic emulsion. This may be explained by different micelle structures existing next to each other. Accordingly, particle measurement and/or a Coulter counter can be used to determine that a so-called "two pack system" of this type consisting of booster and marker leads to two peaks, which allows to conclude that there are different micelle structures extant. In support of this theory, a two pack system of this type generates a higher performance in the application—as compared to a system, in which the performance components were incorporated into a standard concentrate. Equal concentrations need to be considered for comparison in this context.

Lastly, fluorescence measurements on the labelled emulsion systems have also been done.

The analysis device set according to the invention consisting of sample-holding element and analysis apparatus is therefore also very well-suited for the testing of liquids, such as metal processing liquids, cooling lubricants, cooling lubricant emulsions, which contain a booster as well.

In the present case, metal processing liquids shall be understood to include all liquids that are used for lubricating and/or cooling and, if applicable, for rinsing during metal processing processes, such as reforming, or machining processes such as cutting, grinding, lapping, isolating/eroding. Cooling lubricants combining the functions of cooling and lubrication and, if applicable, rinsing are often used in this context. Cooling lubricants can also be used in minimum quantity lubrication. Cooling lubricant emulsions, in turn, relate to correspondingly water-mixed compositions. Although the invention is, particularly advantageously, well-suited for analysis of such metal processing liquids and/or cooling lubricants, and in particular of aqueous cooling lubricant emulsions, it is in no way limited to these. Accordingly, a sample-holding element according to the invention, an analysis device set according to the invention, and a method according to the invention can also be generally used for analysis of any water-containing fluids, for example transmission or hydraulic fluids or aqueous cleaning solutions or emulsions.

The tested liquid is preferred to be a water-containing liquid with a water content ranging from 1 to 99.9%, wherein a water-based liquid with a water content ranging from 1 to 15% is particularly preferred.

Further embodiments as well as some of the advantages associated with these and further embodiments are illustrated and are better comprehensible by the following detailed description with reference to the accompanying figures. Objects or parts thereof that are essentially equal or similar may be denoted by the same reference numbers. The figures are just schematic depictions of exemplary embodiments of the invention.

DESCRIPTION OF PREFERRED EMBODIMENTS

Figure 1:
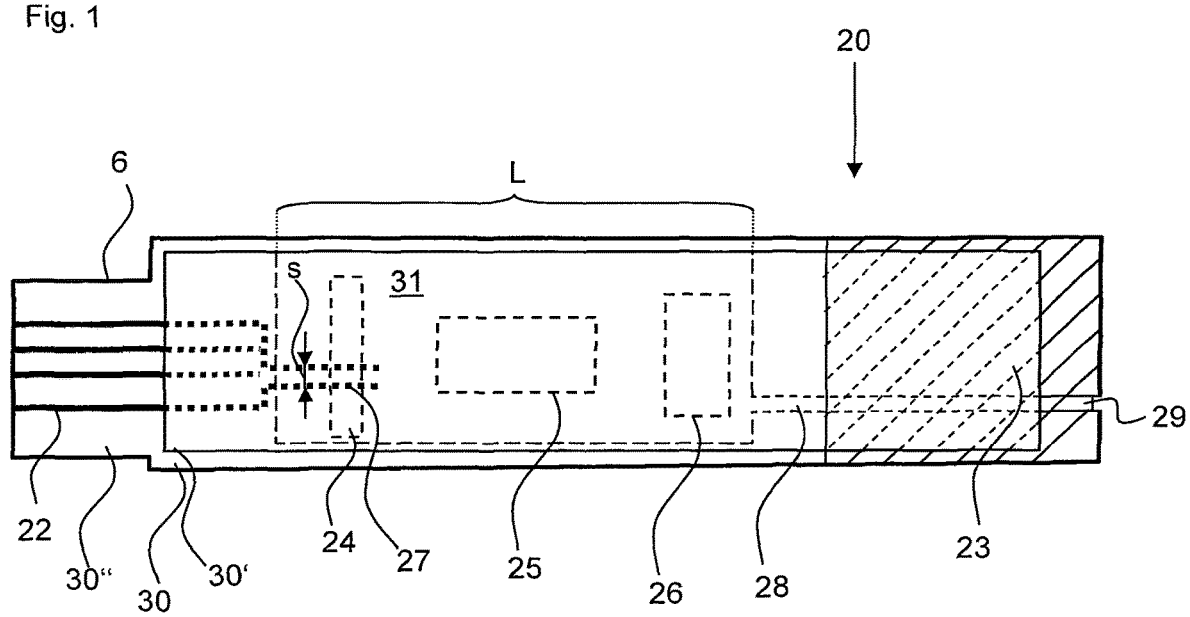
FIG. 1 shows a top view onto a sample-holding element according to the invention.

The analysis device set according to the invention relates to an analysis apparatus designed as a hand-held device for simultaneous determination of various characteristics of a metal processing liquid, in particular of a cooling lubricant, in mobile on-site manner in the production area and/or directly at the tool machine through the use of a special sample-holding element. FIG. 1 shows an exemplary sample-holding element 20 designed as a test strip for single use.

The sample-holding element 20 here is an approximately rectangular planar element that comprises a sample-holding space 31 between two plates 30, 30' in the form of a gap with a planar extension, for the purpose of which the cover plate 30' is connected at its edges to the base plate 30 except for an opening of length L intended for filling, wherein the base plate 30 comprises various functional sections and elements. As shown, the filling opening can be a through-going gap opening extending along a longitudinal edge; depending on the dimensions of the sample-holding element 20, multiple filling openings can be provided just as well through which the sample-holding space 31 is being filled by action of the capillary effect. Accordingly, the distance between the plates 30, 30' is selected to be just so large such that the liquid sample is completely and evenly drawn through the filling opening into the sample-holding space 31 due to the capillary effect. Accordingly, the width of the gap also depends on the dimensions of the sample-holding space 31, but will be in the range of 0.1 to 2 mm, preferably at 0.5 to 1.5 mm, for example approximately 1 mm, in order to form a sample-holding space 31. A suitable dimension for a sample-holding element 20 of, for example, 12×28 mm has been tested.

The sample-holding element 20 that is provided as a test strip in FIG. 1 can therefore comprise a thickness in the range of 2 to 8 mm, preferably in the range of 2.5 to 6 mm, and particularly preferably in the range of 2.5 to 4.5 mm. Moreover, the size and shape of the sample-holding space 31 and therefore of the sample-holding element 20 also depend on the type, number, and space needs of the measuring points 24, 25, 26, 27, which all need to be situated within the plane of the sample-holding space 31 such as to be adjacent to, but also preferably distanced from, each other.

The filling of the sample-holding space 31 is supported by a ventilation channel 28 that extends between the plates 30, 30' to an air exit opening 29—meaning that the plates are not connected to each other in the area of the ventilation channel 28 as well. In the example shown here, the ventilation channel 28 extends from a side of the sample-holding space 31 that is adjacent to the filling gap and through a handle section 23. It is also conceivable to vary the shape, number, and arrangement of the ventilation channels.

The handle section 23 can be ribbed or comprise different textures for improved handling.

Distributed across the sample-holding space 31, the sample-holding element 20 of FIG. 1 comprises three optical measuring points 24, 25, 26 in an adjacent arrangement and one conductivity measuring point 27, which extend, by way of two of their contact strips 22, up into the area of one of the optical measuring points 24 in the present example. Accordingly, three optical measurements A, B, C and one conductivity measurement D can be performed simultaneously with this sample-holding element 20 with the corresponding analysis apparatus 1 (see FIG. 9) after insertion of the liquid-filled sample-holding element 20 through the insertion opening 9 into the analysis apparatus 1.

Figure 8:
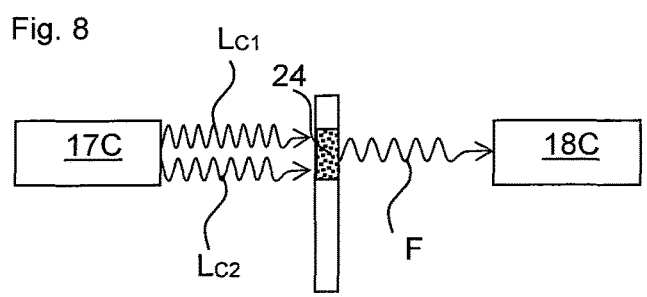
FIG. 8 shows a schematic depiction of a luminometer of the optoelectronic analysis device.

The first optical measuring point 24 is a photonic measuring point, which presently includes all photonic measuring processes, absorption and luminescence measurements. Preferably, the measuring point 24 is intended for luminescence measurement, in particular for fluorescence measurement C, as is schematically depicted in FIG. 8. Monochromatic radiation $L_{C1}$ or $L_{C2}$ from an excitation light source 17C that is part of the hand-held analysis apparatus 1, which is explained in detail below, passes at the measuring point 24 through the liquid sample taken up into the sample-holding space 31, wherein the liquid sample contains a fluorescent marker substance that shows fluorescence shortly after excitation by the radiation $L_{C1}$ or $L_{C2}$. The light emitted in this process is usually lower in energy and consequently has a longer wavelength. Differently from the depiction, the detector 18C detecting the fluorescence radiated power that is proportional to the concentration of the fluorescent substance can just as well be arranged perpendicularly to the axis of the incident light by means of suitable optical elements that are known to a person skilled in the art. Moreover, FIG. 8 indicates, by way of the excitation light beams $L_{C1}$ and $L_{C2}$, that excitation light of different wavelengths can be used for detection of different marker substances. For example, blue light $L_{C1}$ with a wavelength of 450 nm and green light $L_{C2}$ with a wavelength of 530 nm can be used for excitation. Accordingly, a marker can be used that comprises two dye molecules from the series of the rylene dyes such as perylene and quaterrylene (for example Lumogen® F yellow 170, Lumogen® F Pink 285, both available from BASF AG, Ludwigshafen, Germany), or a combination of rhodamine carbonyl derivatives and acridine derivatives (for example ATTO® 612 Q 615 nm and ATTO® 495, 498 nm, both available from ATTO-TEC GmbH, Siegen, Germany), such that the two measuring ranges in the long-wave range can be covered.

On principle, a phosphorescence measurement (with corresponding phosphorescent marker substances) as an alternative to the fluorescence measurement is conceivable just as well. However, whereas fluorescence quickly subsides once the excitation ceases (usually within one millionth of a second), phosphorescence is usually associated with an extended after-glow, up to several hours. Besides a luminescence measuring point, an absorption measuring point for determination of the concentration of certain substances is also conceivable, but the fluorescence measurement has higher selectivity and higher sensitivity as compared to the absorption measurement.

Figure 7:
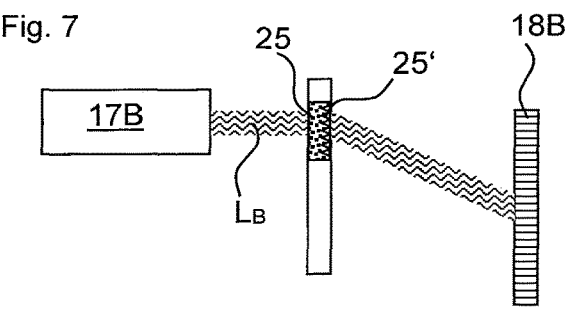
FIG. 7 shows a schematic depiction of a refractometer of the optoelectronic analysis device.

The second optical measuring point 25 of the sample-holding element 20 is provided for measurement of the refractive index B in the present example, wherein one of the plates 30, 30', namely the plate on the light exit side, comprises a prism structure 25' in this section on the inside that is intended as a refractive index measuring point 25, as is indicated schematically in FIG. 7. Said section of the sample-holding element 20 with the prism structure 25' at the measuring point 25, together with the corresponding components of the hand-held apparatus 1, therefore forms the refractometer, which can utilise an energy-saving LED as light source 17B that emits, for example, yellow light $L_B$ with a wavelength of 580 nm. For example, a laser diode can also be utilised as light source as an alternative to an LED. A CCD sensor can be utilised as detector 18B for detection of the refraction of the light beam. Since the refractive index is temperature-dependent, the hand-held apparatus 1 further comprises, for compensation of the temperature influences, a temperature sensor 14, which is connected via a corresponding communication line 33 to the data processing unit 13 of the hand-held apparatus 1 like all other measuring devices of the hand-held device 1.

Figure 6:
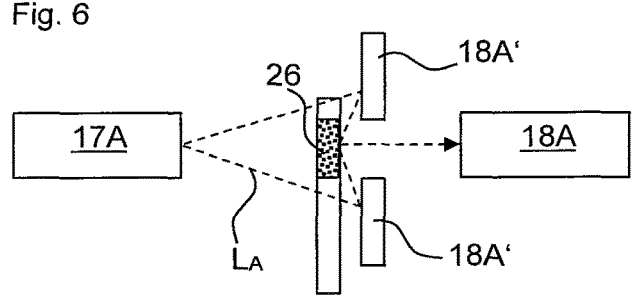
FIG. 6 shows a schematic depiction of an optical pH measuring device of the optoelectronic analysis device.

The sample-holding element 20 from FIG. 1 is shown to have two further measuring points 26 and 27 for pH measurement A and conductivity measurement D. The measuring point 16 is an optical pH measuring point 26, whereby an indicator dye-containing substrate 26' (see FIG. 6) is introduced at this point into the sample-holding space 31 between the two plates 30, 30', whose colour change after contact with the liquid to be tested allows the pH value to be read by optical means. A simple piece of pH paper is conceivable as indicator dye-containing substrate 26'. The measuring components of the hand-held device 1 intended for this purpose can include an RGB-LED as light source 17A, the light $L_A$ of which passes through the sample-holding element 20, past the pH measuring point 26, is diffracted at diffraction devices 18A' and reflected onto the indicator dye-containing substrate 26' in the pH measuring point 26, and, there, only the wavelength of the corresponding colour is reflected, which is then detected by a colour detector 18A and can be used to determine the pH value.

Figure 5:
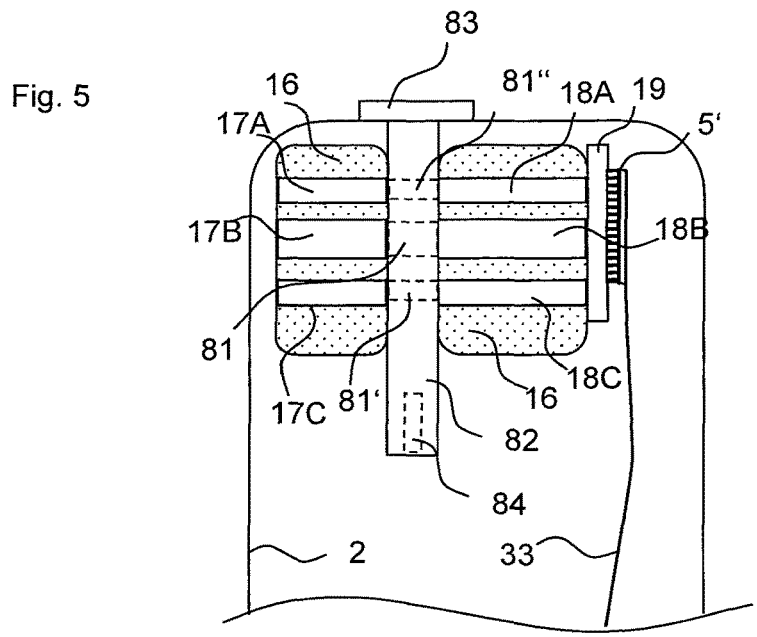
FIG. 5 shows a schematic top view onto a half-shell of the analysis apparatus with insertion device and an optoelectronic analysis device.

All optical measuring components 17A,B,C and 18A,B,C combined form the optoelectronic measuring device 12 of the analysis apparatus 1 (see FIG. 9) and can be arranged in an embedding element 16, as is indicated in FIG. 5. Optical elements, such as filters, lenses, mirrors, etc., that are known for the corresponding measurements A, B, C are not shown here for reasons of clarity. Moreover, FIG. 5 shows a signalling device 19, which at least transmits the signals detected by the detectors and sensors 18A,B,C. Differently from the depiction, an individual signalling device can just as well be provided for each sensor. The signalling device 19 is connected to the data processing unit 13 via the interface 5' and the communication line 33. It is not shown that the light sources 17A,B,C can comprise an appropriate connection for triggering.

Figure 9:
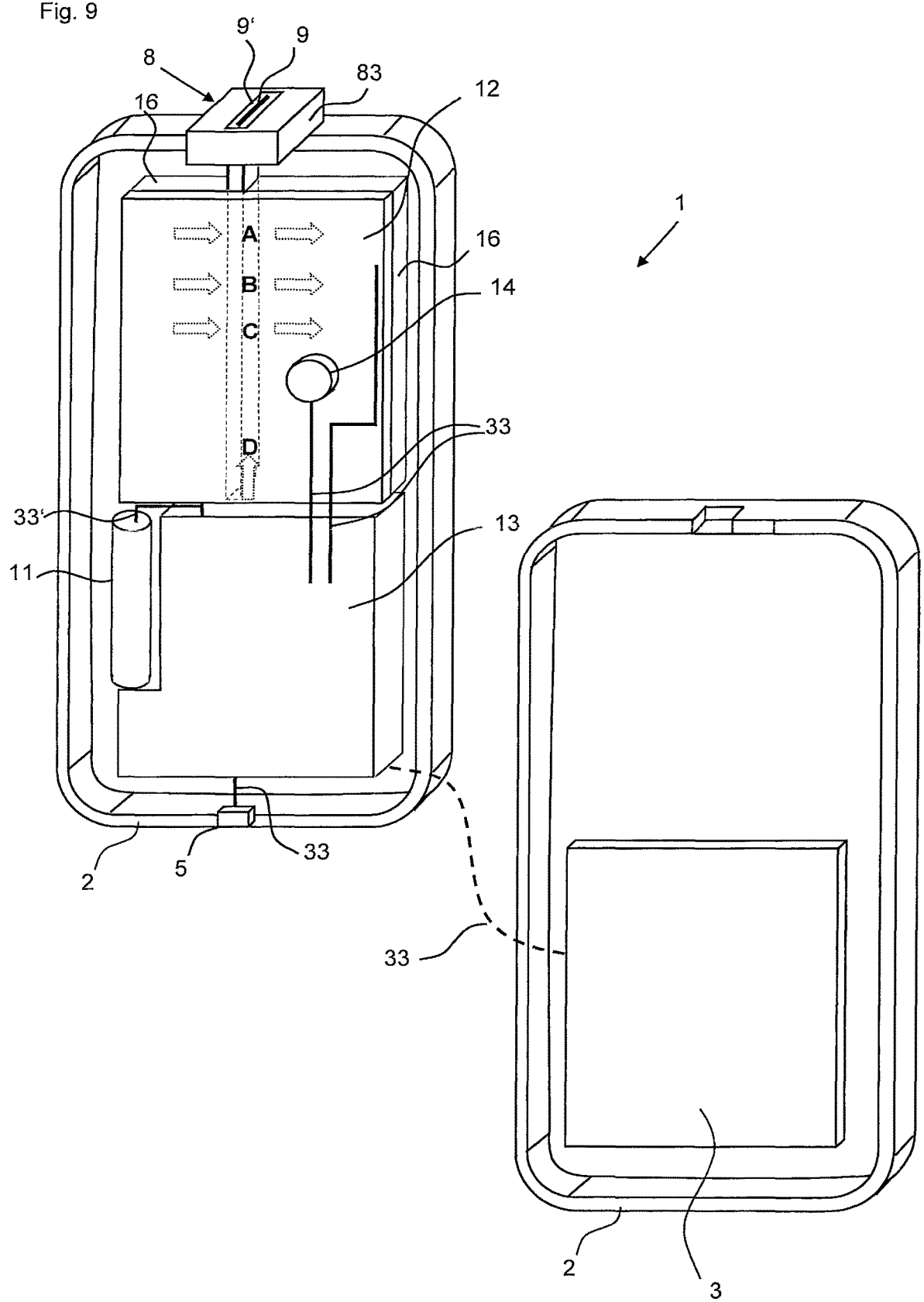
FIG. 9 shows a schematic perspective view of an unfolded analysis apparatus with insertion device.

Moreover, FIG. 9 shows a rechargeable battery 11 as energy source for the supply of electrical energy to all components via power cables 33'. Moreover, the connection of the display device 3, which is arranged in the housing 2 and is preferred to be a touch-screen display, as well as of a (micro) USB interface 5 by means of corresponding communication lines 33 is indicated there. In place of or in addition to a (micro) USB interface 5, a memory card slot or a radio interface (WLAN, Bluetooth®, etc.) can be provided for data transmission from or to an external device. Moreover, the (micro) USB interface can be utilised for recharging the rechargeable battery 11.

The two half-shells forming the housing 2 can be joined to each other, for example, by plug or screw connections and can be opened according to need, for example for replacement of the rechargeable battery 11 or other components. For this purpose, the half-shells can just as well be connected at a longitudinal side by articulated joints, for example by a hinge, such that the plug or screw connections need to be present only on the other side.

Differently from the depiction, instead of a rechargeable battery, a battery can be provided as energy source, which is accommodated for ease of replacement in known manner in a separate compartment that is closed by a section of the housing that can be opened without tools, and comprises contact means for the batteries.

Figure 4:
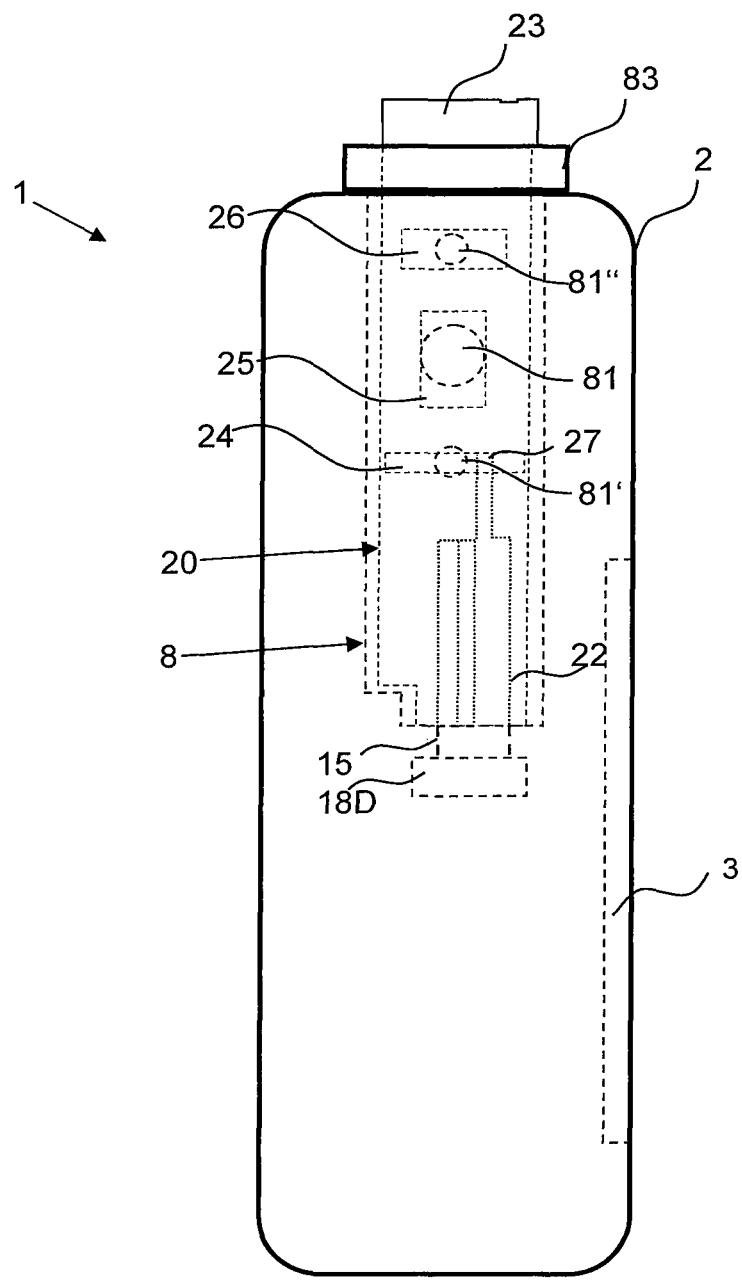
FIG. 4 shows a side view of the analysis apparatus with insertion device and inserted sample-holding element.

For measurement of the conductivity D of the liquid sample, contact strips 22 are arranged at the end of the sample-holding element 20 that faces away from the handle section 23, on a section 30" of the base plate 30 that protrudes longitudinally beyond the end of the cover plate 30'. After insertion of the sample-holding element 20 into the analysis apparatus 1, the free ends of said contact strips 22 can establish an electrically conductive contact to corresponding contact elements 15 of the analysis apparatus 1 (see FIG. 4), such that an alternating current can be applied to the measuring ends of the contact strips 22 by a frequency generator 18D. The measuring ends of the contact strips 22 form the electrodes at the measuring point 27 and are situated at a distance from each other that corresponds to a predetermined measuring section s. The measurement is actually a resistance measurement, from which the conductivity of the liquid can be calculated.

Figure 10:
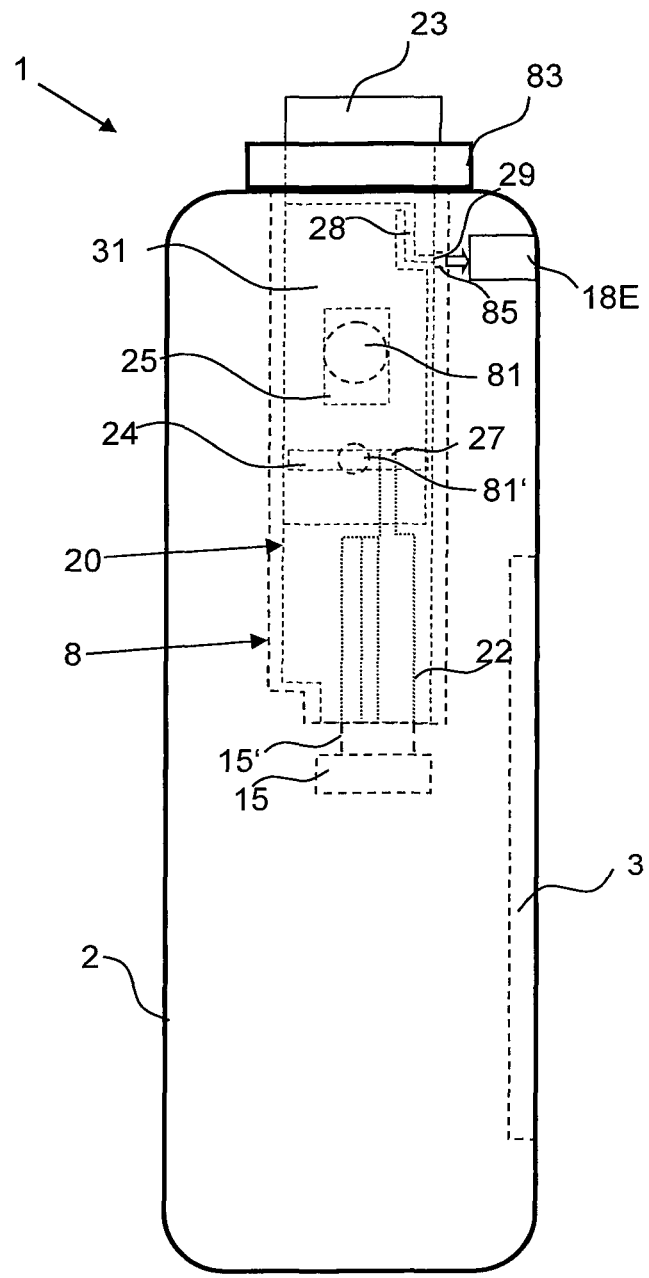
FIG. 10 shows a side view of the analysis apparatus with insertion device and inserted sample-holding element of an alternative embodiment of the analysis device set.

Another conceivable measuring point of the sample-holding element 20 could be a germ measuring point. One example of a germ measurement is shown in FIG. 10. In this context, the ventilation channel 28 is placed appropriately on the sample-holding element 20 such that the air exit opening 29 is not situated in the handle section 23, but rather forms a measuring point that is connected to one or more gas sensors, an "electronic nose", by means of a gas communication facility 85. If applicable, the ventilation channel can comprise changes of cross-section or a bypass supplied air guidance in order to improve the supply of the molecules that are present in the vapour phase of the liquid to the electronic nose. For this purpose, the analysis apparatus can comprise, for example, a fan device. As an alternative to the ventilation channel 28, the extant filling gap can just as well be used as germ measuring point for the "electronic nose". Another approach might be a germ measuring point, in which at least one of the plates 30, 30' comprises a section made of a gas-permeable membrane by means of which the liquid is retained, whereas volatile compounds can pass through and reach the "electronic nose". Said volatile organic compounds are excretion products of the bacteria and/or germs. An "electronic nose" consists, for example, of sensors that are coated with various conductive polymers, which react specifically to various volatile compounds, in that their electrical resistance changes in characteristic manner upon contact with said compounds.

As an alternative to an "electronic nose", germs can just as well be detected by a luminescence measuring cell, if a luciferin/luciferase mixture is added to the liquid that reacts with adenosine triphosphate, which is present in every viable cell. The light emitted in the process can also be measured with the luminometer and is a measure of the microbiological contamination of the liquid.

Depending on the composition of the liquid, a UV absorption measurement can also be conceivable as a further method for germ determination, since nucleic acids absorb in the UV range.

The plates 30, 30' are transparent at least to the corresponding wavelengths at least in the area of the measuring points 24, 25, 26, at which an optical measuring sensory system is applied—for ease of manufacturing, the plates 30, 30' will be completely made of transparent material, which can be glass, preferably quartz glass, or a transparent plastic material. Transparent plastic materials, such as PMMA, are particularly well-suited. A person skilled in the art is aware of suitable plastic materials that can be produced readily in suitable manner by 3-D printing or extrusion.

Besides the desired transparency, the plastic material should be chemically resistant to the ingredients of the liquid to be taken up at least for the time period of sampling and analysis, and preferably should also be electrically insulating in case the sample-holding element 20 comprises a conductivity measuring point. If the plastic material is not electrically insulating to a sufficient degree, the contact strips 22 can be embedded in an insulating material up to the sample-holding space 31. A transparent plastic material that is a good insulator and is resistant to aqueous solutions of neutral salts and oxidation agents as well as to many oils and fats. However, polycarbonates are not resistant to chlorinated hydrocarbons and alkaline aqueous solutions, amines, and ammonia. Polymethylmethacrylate is another transparent plastic material that is resistant to acids, lyes at moderate concentration, petrol and oil, but not to ethanol, acetone, and benzene. Polysulfone is also transparent in the visible range, but it is not resistant to ketones, aromatic compounds, chlorinated hydrocarbons, and polar solvents. Polymethylpentene comprises very high transparency, including in the UV range, but is not permanently chemically resistant to ketones or chlorinated solvents.

The handle section 23, which projects at least partly from the analysis apparatus 1, when the sample-holding element 20 is taken up into the analysis apparatus, can be opaque—as a coloured section of at least one of the plates 30, 30' or as an appended handle section made of a suitable material, for example a plastic material. Preferably, the handle section 23 can be black-coloured in order to prevent and/or minimise the incidence of diffracted light. However, it is conceivable just as well to identify different sample-holding elements 20, which differ in type or intended use, by means of differently coloured and/or differently shaped handle sections 23.

Moreover, markings may be provided on the handle section 23 or in other places of the sample-holding element 20 in order to display to and simplify for a user the correct insertion of the sample-holding element 20 into the analysis apparatus 1. For the same purpose, the sample-holding element 20 can have a back-cut 6, which is unsymmetrical with respect to the longitudinal axis of the sample-holding element 20, at the end (with the contact strips 22) facing away from the handle section 23, such that the sample-holding element can be inserted correctly into the analysis apparatus 1 up to a limit stop in one orientation only to allow the measuring points 24, 25, 26, 27 to communicate with the corresponding measuring devices.

It is self-evident that embodiments deviating in shape and arrangement from the examples given are also included in the scope of protection of the invention. Accordingly, a sample-holding element can just as well have a shape that deviates from an approximately rectangular shape; however, said shape is favourable for a space-saving arrangement of the measuring points and components required for the measurement in the analysis apparatus.

Obviously, in a conceivable embodiment of the analysis device set according to the invention, a sample-holding element 20 can be accommodated directly in an appropriately dimensioned recess of an analysis apparatus 1. However, according to the invention, it is advantageous to provide an insertion device 8 of the type shown in FIGS. 2 to 5, 9, and 10 for this purpose.

Figure 3:
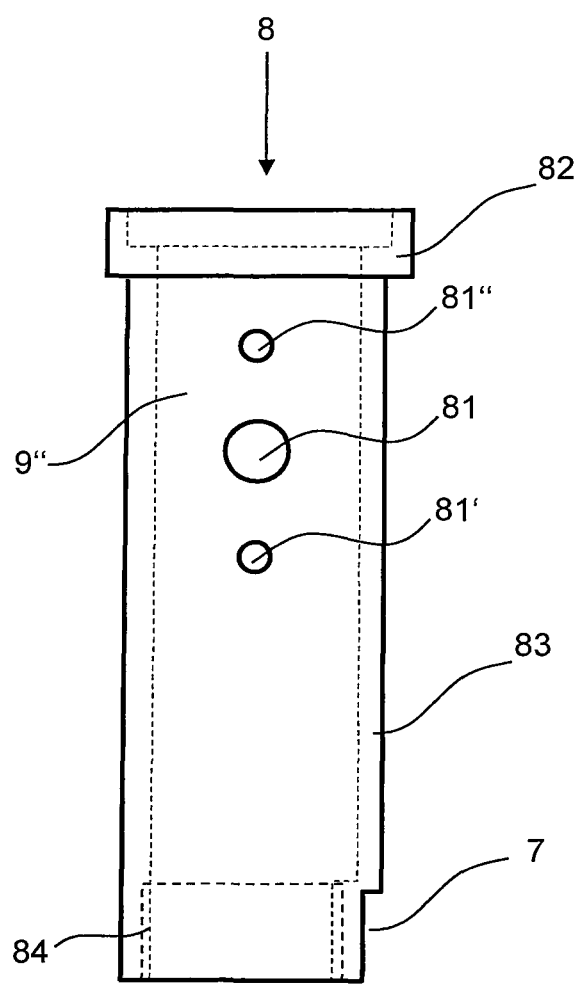
FIG. 3 shows a side view of the insertion device.

The insertion device 8 is fastened in detachable manner in the analysis apparatus 1 such that it can be replaced according to need. The insertion device 8 consists of a shell section 82 that extends on the inside of the analysis apparatus 1, and a flange section 83 that touches on the outside against the edge of the housing 2 of the analysis apparatus 1. The flange section 83 has a slit-like insertion opening 9 in it, from which the recess 9" for the sample-holding element 20 extends through the shell section 82. As is shown in FIG. 3, the latter comprises a back-cut 7 that matches the back-cut 6 of the sample-holding element 20. Also matching the sample-holding element 20 and the measuring devices in the analysis apparatus 1, openings or transparent sections are provided as optical communication facilities 81, 81', 81" in both sides of the otherwise opaque, preferably black, shell section 82, which is intended to prevent and/or reduce effects of diffracted light here as well.

Figure 2:
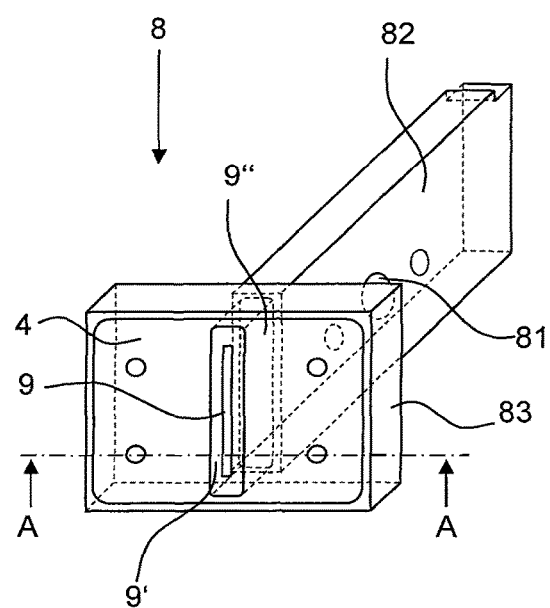
FIG. 2 shows a perspective top view onto an insertion device of an analysis apparatus according to the invention.
Figure 2A:
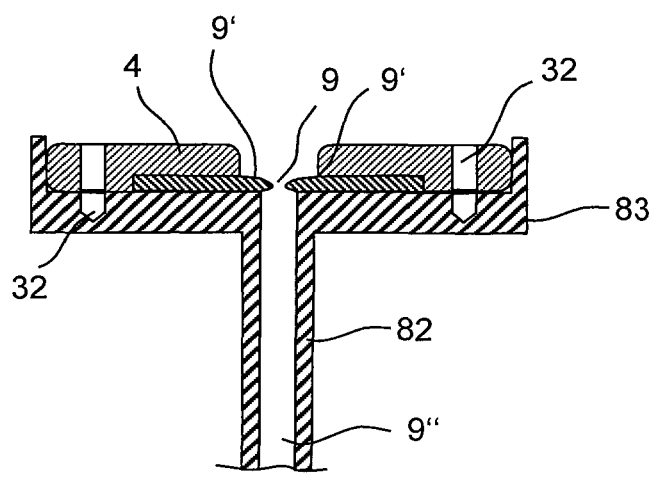
FIG. 2a shows a schematic sectioned side view along AA in FIG. 2.

In the flange section 83, which is shown in a section in FIG. 2a also, a cover plate 4 keeps a sealing lip 9' made of silicone at the insertion opening 9. Boreholes 32 permitting the cover plate 4 to be screwed to the flange section 83 extend through the cover plate 4 and the section of the flange section 83 that is parallel to it. Unlike what is shown in the depiction, the boreholes 32 in the flange section 83 can just as well be through-holes such that not only can the cover 4 be fastened to the flange section 83, but also the latter can be fastened to the edge of the housing 2 of the analysis apparatus 1 in detachable manner. Alternatively, the insertion device 8 can be designed simply for insertion/snap-in into the analysis apparatus 1.

The sealing lips 9' prevent the recess 9" in the shell section 82 from being contaminated. In turn, the insertion device 8 prevents the internal space of the analysis apparatus 1 from being soiled or contaminated.

Moreover, the invention can provide the analysis apparatus 1 to comprise a cover that can be opened (not shown) and can be used to additionally cover the insertion opening 9. A cover of this type can be closed even when the sample-holding element is inserted such that, by this means, the incidence of diffracted light can be prevented and colouring of the handle section can be omitted.

Moreover, the insertion device 8 can comprise, at the end facing away from the flange section 83, in and/or on the section 30" of the sample-holding element 20 with the contact strips 22, when the sample-holding element 20 is inserted into the recess 9" of the insertion device 8, electrical bridging elements that establish an electrical contact between the contact strips 22 of the sample-holding element 20 and the contact elements 15 of the frequency generator 18D, or the insertion element 8 comprises in said place an expansion 84 shaped as a socket in which the plug-like contact elements 15 of the frequency generator 18D can be accommodated such that a direct electrical contact between the contact strips 22 of the sample-holding element 20 and the contact elements 15 of the frequency generator 18D is established.

Figure 11:
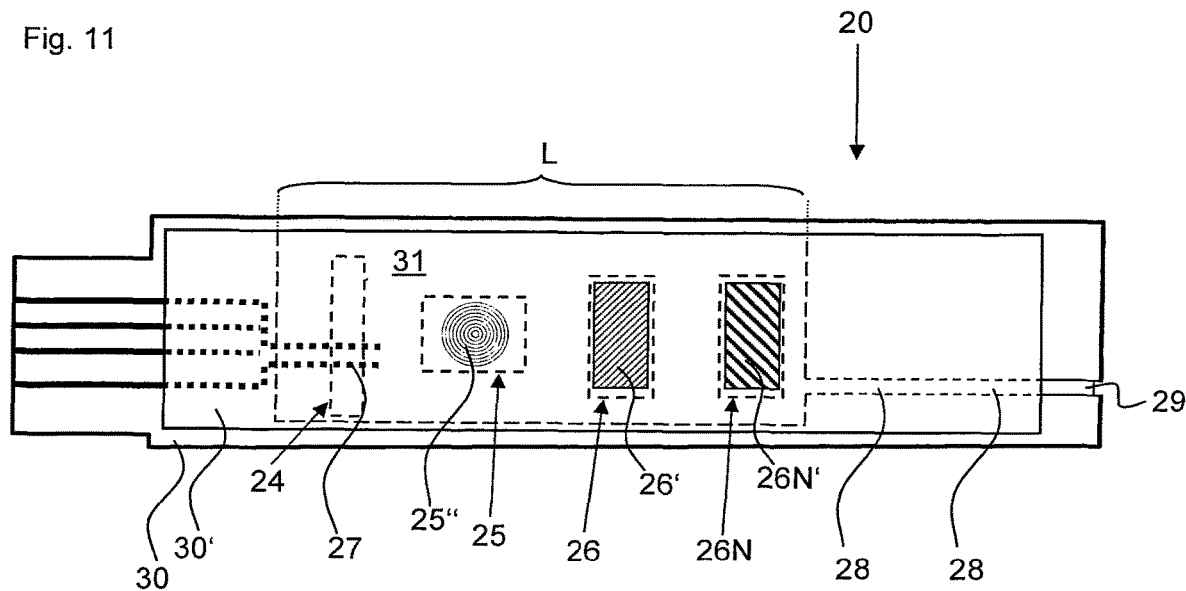
FIG. 11 shows a top view onto a sample-holding element according to the invention with an additional nitrite measuring point.

An alternative embodiment of a sample-holding element 20 is shown in FIG. 11. In addition to the measuring points 24, 25, 26, and, if applicable, 29 for measurement of the conductivity, refractive index, pH, and, if applicable, germs, the sample-holding element 20 comprises an additional nitrite measuring point 26N in the present example, wherein this is a predetermined section between the plates 30, 30', into which a nitrite-reactive substrate 26N' has been introduced that performs a reaction with nitrite that can be detected, for example, photometrically and can be quantified by calibration such that, similar to the pH measuring point 26, a colour change can be detected optoelectronically by means of which the presence and quantity of nitrite in the tested liquid can be detected.

The sample-holding element 20 from FIG. 11 differs further in the type of the diffraction structure of the measuring point 25 that is used for determination of the refractive index. Whereas the diffraction structure described in the context of the example according to FIG. 7 is a prism structure 25' that consists of multiple structures arranged adjacently to each other having a triangular profile, for example pyramidal or tetrahedral structures or parallel-extending triangular profiles on the inside of the plate 30, 30' on the light exit side, the refractive index measuring point 25 of the sample-holding element 20 from FIG. 11 comprises a Fresnel lens structure 25" as diffraction structure which—also on the inside of the plate 30, 30' on the light exit side—consists of a series of ring-shaped steps.

Figure 12:
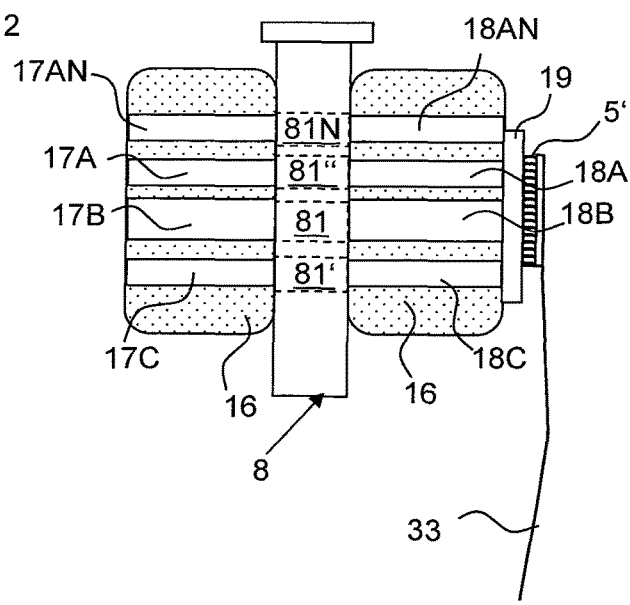
FIG. 12 shows a schematic top view onto an optoelectronic analysis device of the analysis apparatus with insertion device for the sample-holding element from FIG. 11.

In FIG. 12, an insertion element 8 matching the sample-holding element 20 from FIG. 11 is inserted into the embedding element 16 of an analysis apparatus that is not shown in any further detail. Unlike the example shown in FIG. 5, the insertion element 8 comprises, as optical communication facilities 81N, a further opening or a transparent sections in both sides of the otherwise opaque, preferably black, shell section 82 matching the additional nitrite measuring point 26N of the sample-holding element 20 as shown in FIG. 11 in order to prevent and/or reduce the effects of diffracted light here as well. For measurement of the nitrite content, measuring optics 17AN, 18AN that can match the measuring device for pH measurement 17A, 18A are incorporated in appropriate place in the embedding element 16. As before, an RGB-LED, as light source 17AN, and a colour detector 18AN can be used.

As before, the signal detected by the sensor and/or colour detector 18A is transmitted by the signalling device 19 via the interface 5' and the communication line 33 to the data processing unit.

The measuring components of the refractometer can remain unchanged and can be formed, for example, by a (LED or laser diode) light source 17B and a CCD sensor 18B.

It is an essential aspect of the invention that the concentration of the manufacturing medium and/or cooling lubricant in the emulsion comprises an internal marker substance, i.e. a dye, that shows fluorescence after excitation with light of a suitable wavelength. As a supplement, the single sample-holding element is used simultaneously to also measure the conductivity parameter, the pH value, and the refractive index, from which conclusions concerning the concentration can be made as well, in a single analysis apparatus that is designed as a hand-held device, by means of a single sampling in one measuring process.

Differently from large stationary analysis systems, which can also detect a large range of characteristic data, but can work economically only with a large number of identical samples, the analysis device set according to the invention permits the economical use with different special emulsions that are produced only on a limited scale, for example in small series, whose processing is subject to special requirements. Accordingly, the analysis apparatus, whose luminometer comprises lasers with (at least) two different excitation wavelengths, can be used for detecting the concentration not only of a conventional cooling lubricant to which a marker substance has been added and/or a corresponding emulsion, but also of a so-called "two pack system". In this context, a booster additive is added to a conventional cooling lubricant emulsion during the production process in order to increase the performance, usually at a concentration of less than approximately 5% by weight, which is the case especially when, for example, small series' with particular quality requirements need to be included into the standard manufacturing process. In this case, the performance of conventional cooling lubricants in common use is insufficient such that, as a consequence, the tool machine(s) would need to be converted to a different cooling lubricant with a higher performance, which would lead to an increased variety of cooling lubricant types and would be uneconomical. Therefore, the booster additive imparting advantageous additional properties to the cooling lubricant, for example with respect to the dispersing capacity, wear protection and/or change of friction coefficient, is added to the conventional cooling lubricant. However, if a booster additive is added, it is important to test the concentration thereof for quality assurance purposes, wherein only the ingredients contained in the booster additive and not those of the cooling lubricant are to be detected.

Hitherto, it was possible to implement booster concentration measurements only with much effort in the laboratory by means of infrared spectroscopy and X-ray fluorescence analysis. It has now been evident, surprisingly, that a specific selection of the marker substance allows the booster to be "doped" appropriately such that this marker substance does not "diffuse into" the basic cooling lubricant. Theoretically, there are basically two different emulsion systems present in parallel, wherein the determination of the concentration of the basic cooling lubricant takes place by means of a first marker substance and the determination of the concentration of the booster additive takes place by means of the second marker substance. Accordingly, an unambiguous determination of the concentration of the booster additive as well is feasible on-site, which could not be realised previously.

It is self-evident that the determination of the concentration of the cooling lubricant and booster additive in an emulsion after addition of a marker substance to each by means of fluorescence measurement of the different marker substances can just as well be carried out through other analysis devices than the analysis device set according to the invention—however the latter advantageously offers an inexpensive and rapid analysis directly on-site.

A measuring process that can be carried out with the analysis device set according to the invention can have a workflow as follows:

After the analysis apparatus 1 is switched on, which can take place in common manner by keeping a colour-coded key on the housing 2 pressed, the touch-screen display 3 becomes active—if applicable, a control lamp next to the key may light up—and a selection menu showing the various liquid media that can be tested appears on the display 3, in particular cooling lubricant emulsions that are deposited in a database that is stored in the data processing unit or on a storage medium (non-removable or removable storage medium) connected to the data processing unit. The liquid to be tested can be selected by touching the touch-screen display 3.

The sampling of the liquid to be tested can take place by immersing the sample-holding element 20 by the filling opening into the liquid—or it may be sufficient to contact the filling opening to the liquid surface—whereby the sample-holding space 31 gets filled with the liquid due to the action of the capillary effect. The period of time for this purpose is usually a few seconds and can vary depending on the selected dimensions of the sample-holding element 20, until the sample-holding space 31 is completely filled with the liquid due to the action of the capillary effect, wherein any air that may be present can escape through the ventilation channel 28.

The cooling lubricant emulsion and/or the liquid should be well-mixed during the sampling. Therefore, the liquid may need to be mixed prior to sampling in order to assure a homogeneous distribution of the cooling lubricant in the emulsion. As an alternative to immersing and/or holding to the liquid surface, a pipette or similar sampling means can be used just as well in order to draw a sample of the liquid, which is then filled at the filling opening into the sample-holding space 31 of the sample-holding element 20. If the immersion or filling process causes liquid to adhere to the outside surface of the sample-holding element 20, this and other soiling is removed before insertion of the sample-holding element 20 into the analysis apparatus 1.

The sample-holding element 20 held by the handle section 23 is inserted, with the section 30" leading, through the insertion opening 9 into the recess 9" that is designed as a measuring channel. The sealing lip 9' at the insertion opening 9 prevents contamination of the measuring channel, which is surrounded by the shell section 82, of the insertion device 8, which can be replaced according to need, which prevents the internal space of the analysis apparatus from being contaminated.

Upon completion of the insertion process, when the contact strips 22 on the lengthened section 30" of the sample-holding element 20 contact the contact elements 15 of the analysis apparatus 1, the measuring process is started automatically. If an automatic start of the measuring process is not desired, the invention can provide for a user input, for example pressing of a corresponding message displayed on the touch-screen display 3.

After completion of the measurement(s), a prompt for removal of the sample-holding element 20 is shown on the touch-screen display 3. Once this is done, the measured values are displayed. The sample-holding element 20 designed as a test strip for single use can be discarded.

Although it is conceivable, on principle, that the two plates 30, 30' constituting the sample-holding element can be detached from each other for cleaning of the internal space and renewal of the pH indicator substrate, this is uneconomical.

The measured values can be stored in the data processing unit 13 and/or a storage medium connected to it. Moreover, the measured values can be transmitted to an external data processing facility and/or a storage unit by means of a wireless radio connection, e.g. according to the Bluetooth® standard. For this purpose, an appropriately identified field is displayed on the touch-screen display 3, which, when activated, establishes a pre-set radio connection and transmits the measured values. After completion of the data transmission, said connection is disconnected automatically or can be terminated through another user input.

Much like switching the analysis apparatus 1 on, switching it off can require pressing the key for a predetermined period of time, e.g. until the control lamp shuts off; but automatic switch off according to a pre-set timer can take place just as well.

The analysis apparatus 1 can be used not only to analyse the known liquids deposited in the database, but it is also feasible to perform a calibration and new liquids/cooling lubricants can be inputted, which are then added to the database.

For calibration, the user has to actuate a correspondingly identified field in the start menu on the touch-screen display 3, upon which a calibration menu opens that comprises pertinent control fields for calibration of the analysis apparatus for measurement of the parameters that can be tested, refractive index, pH value, and conductivity. For calibration purposes, the analysis device set comprises different calibration solutions, for example in pipette flasks that are provided in a separate box.

Moreover, the calibration menu comprises appropriately identified control fields that can be activated to input new liquids/cooling lubricants labelled with a marker substance and/or to recalibrate media entered previously. Appropriate fluorescence-labelled liquids/cooling lubricants are required for this purpose. For recalibration, the analysis device set can provide a demonstration solution with a fluorescence-labelled cooling lubricant.

An analysis device according to the invention that is intended for analysis of cooling lubricants and/or cooling lubricant emulsions can be designed for the following measuring ranges:

Refractive index from 1.333 to 1.38 (0 to 30 Brix)
pH value from 7 to 10
Conductivity from 0.2 to 6 mS/cm
Cooling lubricant concentration in the emulsion from 0 to 15% by weight or at least in the range of 0 to 10% by weight, if applicable from 0 to 5% by weight For a different liquid, the analysis device set can just as well be designed for other measuring ranges.

LIST OF REFERENCE NUMBERS

| | |
|---|---|
| 1 | Analysis apparatus |
| 2 | Housing |
| 3 | Display device |
| 4 | Cover |
| 5, 5' | External/internal interface |
| 6, 7 | Back-cut |
| 8 | Insertion device |

-continued

| | |
|---|---|
| 81, 81', 81", 81N | Communication facility |
| 82 | Shell section |
| 83 | Flange section |
| 84 | Socket/opening for contact |
| 85 | Gas communication facility |
| 9 | Insertion opening |
| 9' | Sealing lip |
| 9" | Recess |
| 11 | Rechargeable battery |
| 12 | Optoelectronics |
| 13 | Data processing unit |
| 14 | Temperature sensor |
| 15 | Contact element |
| 16 | Embedding element |
| 17A, B, C, AN | Light source |
| 18A, B, C, AN | Detector, sensor |
| 18A' | Diffraction device |
| 18D | Frequency generator |
| 18E | Gas sensor |
| 19 | Signalling device |
| 20 | Sample-holding element |
| 22 | Contact strip |
| 23 | Handle section |
| 24 | Measuring point for fluorescence measurement (concentration) |
| 25 | Measuring point for refractive index measurement |
| 25' | Prism structure |
| 25" | Fresnel lens structure |
| 26 | Measuring point for pH measurement |
| 26' | Indicator substrate |
| 26N | Nitrite measuring point |
| 26N' | Nitrite-reactive substrate |
| 27 | Measuring point for conductivity measurement |
| 28 | Channel |
| 29 | Air exit opening |
| 30, 30' | Plates |
| 30" | Lengthened plate section for contact strip |
| 31 | Sample-holding space |
| 32 | Bore hole |
| 33 | Communication line |
| 33' | Energy supply line |
| L | Length of filling gap |
| s | Measuring section |

What is claimed is:

1. A sample-holding element (20) for a liquid sample for simultaneous analysis of three or more chemico-physical parameters of the liquid, the sample-holding element (20) comprising:
  a sample-holding space (31) that can be filled with the liquid;
  at least three measuring points (24, 25, 26, 26N, 27) in adjacent arrangement with respect to each other distributed across the sample-holding space (31), wherein two of the measuring points (24, 25) are a photonic measuring point (24) and a refractive index measuring point (25), and wherein the at least one further measuring point is selected from the group consisting of at least one pH measuring point (26), one conductivity measuring point (27), and one germ measuring point;
  wherein the sample-holding element (20) is a planar element (20) that is double-walled at least in sections and comprises two planar-parallel plates (30, 30') arranged on top of each other that are connected to each other, wherein the sample-holding space (31) is designed in the form of a gap in planar manner between the two plates (30, 30');
  wherein the plates (30, 30') are connected to each other at least in sections at their edges, wherein an opening of the sample-holding element (20) is formed by the non-connected parts of the edge, and a distance between the plates (30, 30') is just so large that the liquid sample between the double walls (30, 30') can be subjected to the capillary effect;
  wherein the measuring point (25) for the refractive index measurement comprises a prism structure (25', 25") at one of the plates (30, 30') in a predetermined area, wherein the plates (30, 30') are transparent in the predetermined area to the wavelengths used for the refractive index measurement, wherein the prism structure (25', 25") provides surface sections that are angled with respect to the plate plane, at which incident light beams are refracted accordingly.

2. The sample-holding element (20) according to claim 1, wherein the plates (30, 30') are not connected to each other at least along one side such that a filling opening or a filling gap with a length (L) for the liquid is provided.

3. The sample-holding element (20) according to claim 1, wherein the planar element (20) consists, at least in part, of translucent glass material or a transparent plastic material.

4. The sample-holding element (20) according to claim 1, wherein the length of one of the two plates (30) is larger, at least on one end, than the length of the other plate (30') and comprises a section (30") on which at least two contact strips (22) for the application of voltage are arranged and extend into the sample-holding space (31) and end there at a distance from each other, wherein the distance corresponds to a measuring section (s) that forms the measuring point (27) for the conductivity measurement.

5. The sample-holding element (20) according to claim 4, wherein the planar element (20) is designed, at another end that faces away from the end with the contact strips (22), in the form of a handle section (23) for handling of the sample-holding element (20),
  wherein a fluid path extends from the filling opening or the filling gap of length (L) along the measuring points (24, 27, 25, 26, 26N) to a ventilation channel (28) that terminates at an air exit opening (29) on the outside of the planar element (20).

6. The sample-holding element (20) according to claim 1, wherein
  the photonic measuring point (24) is a luminescence measuring point (24), wherein the plates (30, 30') are transparent to the excitation and emission wavelengths of the intended luminescence measurement at a predetermined first section.

7. The sample-holding element (20) according to claim 1, wherein the measuring point for the pH measurement (26) comprises an indicator dye-containing substrate (26') that is arranged at a predetermined second section between the two plates (30, 30').

8. The sample-holding element (20) according to claim 1, wherein the prism structure (25') is formed by at least one structure with a triangular profile in an adjacent arrangement or a Fresnel lens structure (25") that comprises a series of ring-shaped steps and is provided at a predetermined third section of one of the two plates (30, 30').

9. The sample-holding element (20) according to claim 1, wherein the at least three measuring points (24, 25, 26, 26N, 27) further include a nitrite measuring point (26N) that comprises a nitrite-reactive substrate (26N') that is arranged at a predetermined fourth section between the two plates (30, 30').

10. An analysis device set for simultaneous analysis of at least three different chemico-physical parameters of liquids;
  wherein the analysis device set comprises
  an analysis apparatus (1) designed as a hand-held device with a housing (2) and with a display device (3), at least one sample-holding element (20) according to claim 1 for a liquid sample;

wherein the analysis apparatus (1) comprises an optoelectronic analysis device (12) and a data processing unit (13) that is connected in communicative manner to the analysis device (12) and the display device (3), wherein the optoelectronic analysis device (12) comprises at least three measuring devices (15, 17, 18) in an adjacent arrangement with respect to each other, whose arrangement matches the arrangement of the measuring points (24, 25, 26, 26N, 27) on the sample-holding element (20).

11. The analysis device set according to claim 10, wherein the analysis apparatus (1) comprises an insertion device (8) for accommodation of the sample-holding element (20), the insertion device arranged in the housing (2) in a detachable manner and comprising an insertion opening (9) that terminates in a recess (9") for accommodating the sample-holding element (20) that is correspondingly designed, wherein the insertion device (8) comprises an optical, electronic or optoelectronic communication facility (81, 81', 81", 81N) that matches the arrangements of the measuring devices (15, 17, 18) and measuring points (24, 25, 26, 26N, 27) depending on the type of the respective measuring point (24, 25, 26, 26N, 27).

12. The analysis device set according to claim 11, wherein the insertion device (8) comprises a flange section (83) with the insertion opening (9) and a shell section (82) that is arranged in the housing (2) such as to be detachable, borders the recess (9") and comprises the optical, electronic or optoelectronic communication facilities (81, 81', 81", 81N) that are formed by sections made of transparent material and/or by openings in the shell section (82), which otherwise is manufactured from opaque material.

13. The analysis device set according to claim 12, wherein the flange section (83) of the insertion device (8), in an analytical arrangement, in which the insertion device (8) is inserted into the housing (2), touches, on the outside, against an edge of the housing (2) and frames a cover plate (4), in which the insertion opening (9) has been made, which is sealed by a sealing lip (9') that is held in the flange section (83) by the cover plate (4), wherein the cover plate (4) is detachably fastened in the flange section (83).

14. The analysis device set according to claim 13, wherein the insertion device (8) comprises contact bridges that establish the contact of the contact elements (15) of the analysis apparatus (1) to the at least two contact strips (22) of the sample-holding element (20).

15. The analysis device set according to claim 10, wherein two of the measuring devices (15, 17, 18) are a a luminescence measuring device (17C, 18C), and a refractive index measuring device (17B, 18B), and wherein the at least one further measuring device (15, 17, 18) is selected from the group comprising at least one pH measuring device (17A, 18A), one conductivity measuring device (15, 18D), one nitrite measuring device (17AN, 18AN), and one measuring device (18E) for detection of the germ load, the luminescence measuring device (17C, 18C), the refractive index measuring device (17B, 18B), the pH measuring device (17A, 18A), and the nitrite measuring device (17AN,18AN) each comprise a light source unit (17A, 17B, 17C, 17AN) and a detection unit (18A, 18B, 18C,18AN) that are arranged in the housing (2) on both sides of the corresponding measuring points (24, 25, 26, 27, 26N) of the sample-holding element (20) accommodated in the analysis apparatus (1), wherein the analysis apparatus (1) comprises a temperature measuring device (14) that is connected to the data processing unit (13);

the conductivity measuring device (15, 18D) comprises a frequency generator (18D) with contact elements (15), which are in electrical contact with the at least two contact strips (22) of the sample-holding element (20) when the sample-holding element (20) is arranged in the analysis apparatus;

the measuring device (18E) for detection of the germ load is at least one microelectronic gas sensor (18E) that is connected to the sample-holding space (31) by a connecting line.

16. The analysis device set according to claim 10, wherein the analysis device (1) comprises an energy source, which is arranged in the housing (2) and provides the energy supply of the optoelectronic analysis device (12), of the data processing unit (13), and of the display device (3).

17. The analysis device set according to claim 10, wherein:

the display device (3), as a control interface, is a touch-sensitive display device (3), the data processing unit (13) comprises or is connected to an external communication interface (5), wherein the external communication interface (5) is a plug contact interface or a radio interface.

18. A method for simultaneous analysis of at least three different chemico-physical parameters of a liquid by using an analysis device set according to claim 10, the method comprising the steps of:

immersing the sample-holding element (20) into the liquid or contacting an opening of the sample-holding element (20) that is formed by the non-connected parts of the edge to the liquid surface, and filling the sample-holding space (31) of the sample-holding element (20) with a sample of the liquid through the action of the capillary effect between the double walls (30, 30') of the sample-holding element (20), completely inserting the sample-holding element (20) into the analysis apparatus (1), starting and carrying out at least three or more measuring processes simultaneously by the measuring devices (18A,B,C,D,E,AN) at the measuring points (24, 25, 26, 27, 28, 26N), after completion of the measuring processes, displaying the measuring results on the display facility (3).

19. The method according to claim 18, wherein various liquids that can be tested are deposited in a database that is stored in the data processing unit or on a storage medium connected to it, and selecting the liquid to be tested through a user input on the display device (3) before starting and carrying out at least three or more measuring processes simultaneously by the measuring devices (18A,B,C,D,E, AN) at the measuring points (24, 25, 26, 27, 28, 26N).

20. The method according to claim 18, further comprising detecting the complete insertion of the sample-holding element (20) into the analysis apparatus (1) automatically or after a user input.

21. The method according to claim 18, further comprising the steps of:

calibrating the analysis apparatus (1) for the liquids that can be tested and are deposited in the database, through the use of calibration solutions, and/or inputting new liquids with known chemico-physical parameters with the analysis apparatus (1) and adding the inputted liquids to the database.

22. The method according to claim 21, wherein the liquid comprises at least one marker substance that can be detected by luminescence analysis, and wherein one of the measuring points (24, 25, 26, 27, 28, 26N) is a luminescence measuring point (24).

23. The method according to claim 22, wherein the liquid to be analysed is a metal processing liquid or a metal processing cooling lubricant, wherein at least one first marker substance that can be detected by luminescence analysis is added to the liquid at a predetermined concentration.

24. The method according to claim 23, wherein the liquid comprises a booster additive and at least one second marker substance that can be detected by luminescence analysis is added to the liquid at a predetermined concentration, wherein the second marker substance differs from the first marker substance with regard to its luminescence properties.

* * * * *